United States Patent
Rainbow

(10) Patent No.: US 11,931,505 B2
(45) Date of Patent: *Mar. 19, 2024

(54) INHALER HOUSING

(71) Applicant: Heath Rainbow, Brisbane (AU)

(72) Inventor: Heath Rainbow, Brisbane (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,131

(22) Filed: Jul. 7, 2022

(65) Prior Publication Data

US 2022/0331530 A1    Oct. 20, 2022

Related U.S. Application Data

(63) Continuation of application No. 16/466,219, filed as application No. PCT/AU2017/051340 on Dec. 6, 2017, now Pat. No. 11,426,539.

(30) Foreign Application Priority Data

Dec. 6, 2016 (AU) .................................. 2016905026

(51) Int. Cl.
*A61M 15/00* (2006.01)

(52) U.S. Cl.
CPC ........ *A61M 15/0026* (2014.02); *A61M 15/00* (2013.01); *A61M 15/0023* (2014.02); *A61M 15/009* (2013.01); *A61M 15/0021* (2014.02); *A61M 2209/088* (2013.01)

(58) Field of Classification Search
CPC ............ A61M 15/0026; A61M 15/009; A61M 15/0023; A61M 15/0021; A61M 15/00
See application file for complete search history.

(56) References Cited

U.S. PATENT DOCUMENTS

| | | | |
|---|---|---|---|
| 2,642,063 A | 6/1953 | Brown | |
| 3,107,670 A | 10/1963 | Silson et al. | |
| 3,184,115 A * | 5/1965 | Meshberg | A61M 15/0023 239/587.5 |
| 3,191,867 A * | 6/1965 | Lee | A61M 15/009 128/200.23 |
| RE26,304 E * | 11/1967 | Meshberg | B65D 83/30 222/530 |
| 3,506,004 A * | 4/1970 | Mann | A61M 15/009 222/533 |
| 3,927,806 A | 12/1975 | Meshberg | |
| 3,994,421 A | 11/1976 | Hansen | |
| 4,069,819 A | 1/1978 | Valentini et al. | |

(Continued)

FOREIGN PATENT DOCUMENTS

| | | |
|---|---|---|
| GB | 946006 A | 1/1964 |
| GB | 1004363 A | 9/1965 |

OTHER PUBLICATIONS

International Search Report from International Application No. PCT/AU2017/051340 dated Apr. 9, 2018.

*Primary Examiner* — Tu A Vo
(74) *Attorney, Agent, or Firm* — Dorsey & Whitney LLP

(57) ABSTRACT

An inhaler housing comprising a receiving portion adapted to at least partially receive a container containing a medicament, and a dispensing portion through which the medicament is dispensed, wherein the receiving portion and the dispensing portion are movable relative to one another between a storage condition in which the receiving portion and the dispensing portion at least partially overlie one another and a use condition.

16 Claims, 8 Drawing Sheets

(56) References Cited

U.S. PATENT DOCUMENTS

| | | | |
|---|---|---|---|
| 4,509,515 A * | 4/1985 | Altounyan | C08G 18/10 |
| | | | 128/200.23 |
| 4,637,528 A | 1/1987 | Wachinski et al. | |
| 4,641,644 A | 2/1987 | Andersson et al. | |
| 4,896,832 A | 1/1990 | Howlett | |
| 5,505,194 A | 4/1996 | Adjei et al. | |
| 5,785,048 A * | 7/1998 | Koerner | G01G 1/24 |
| | | | 128/200.23 |
| 6,230,704 B1 | 5/2001 | Durkin et al. | |
| 6,360,929 B1 | 3/2002 | McCarthy | |
| 11,426,539 B2 * | 8/2022 | Rainbow | A61M 15/0026 |
| 2002/0121276 A1 | 9/2002 | Genova et al. | |
| 2008/0087279 A1 | 4/2008 | Tieck et al. | |
| 2008/0251551 A1 | 10/2008 | Huber et al. | |
| 2014/0174441 A1 | 6/2014 | Seeney et al. | |
| 2014/0190473 A1 * | 7/2014 | Haindl | A61M 15/004 |
| | | | 128/200.14 |
| 2016/0022933 A1 | 1/2016 | Ciancone et al. | |

\* cited by examiner

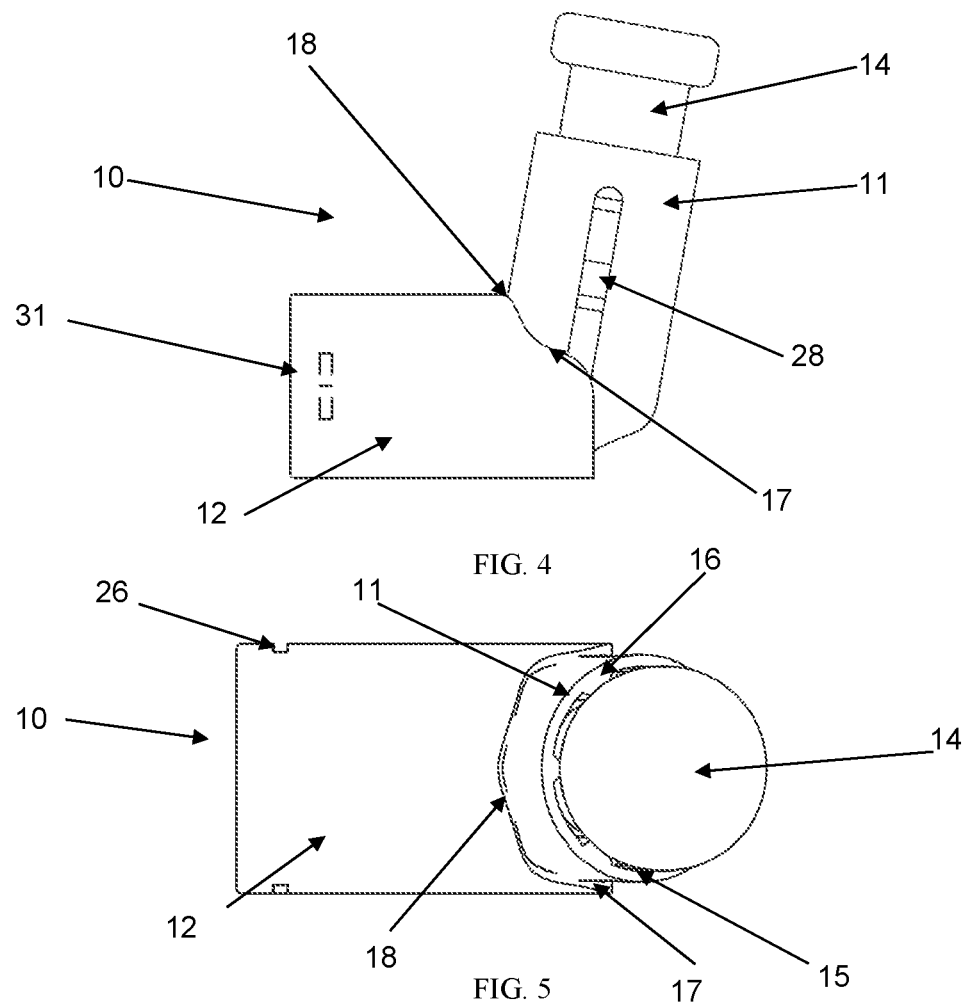
FIG. 4
FIG. 5
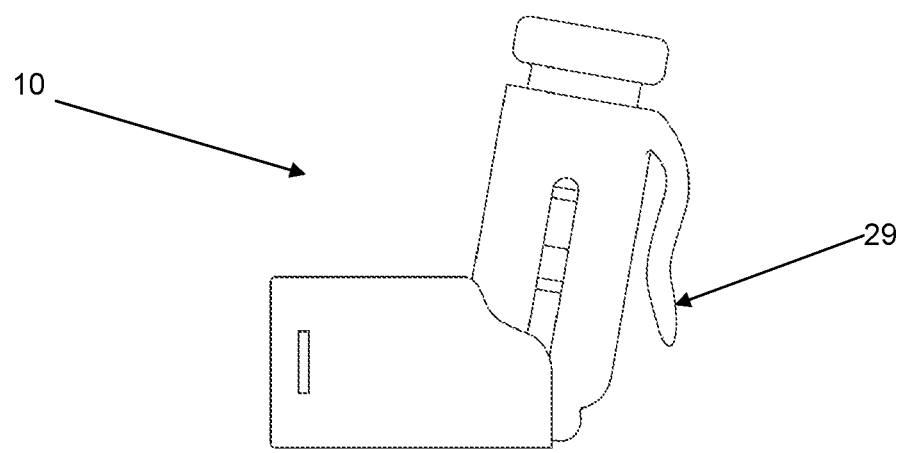
FIG. 6

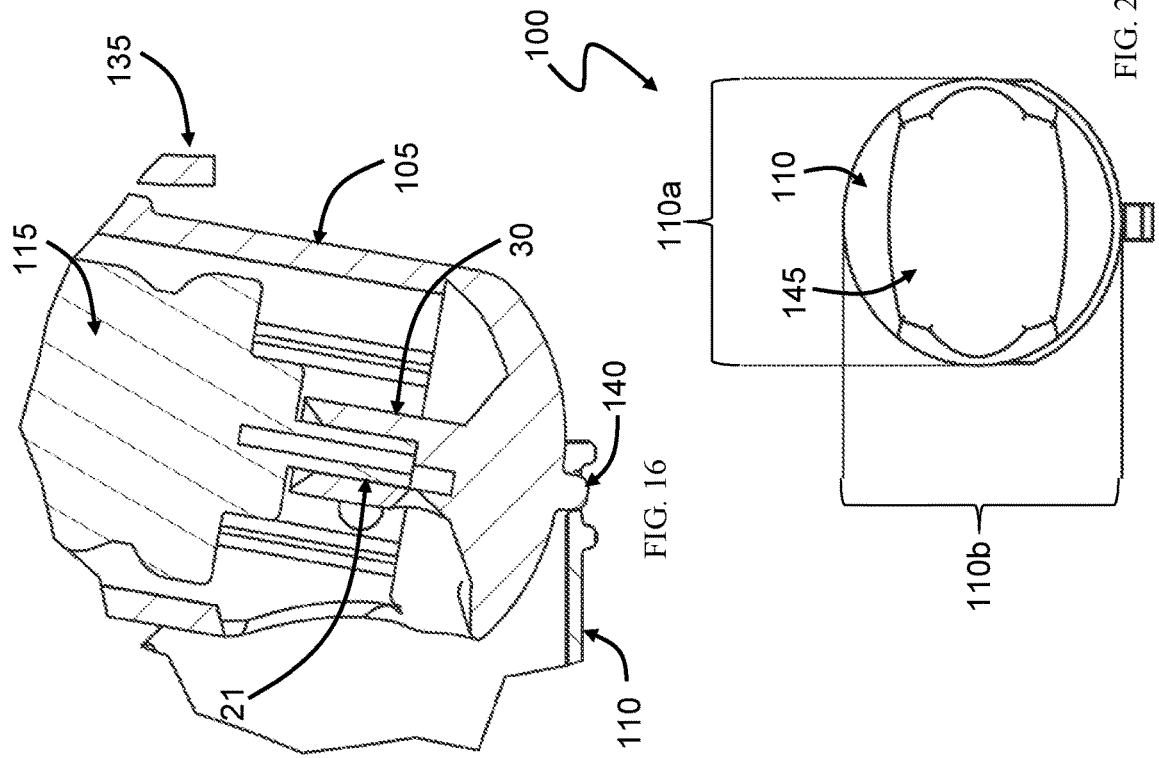
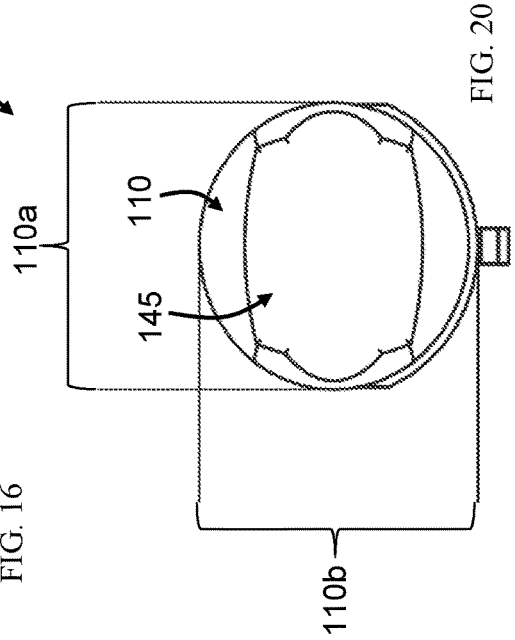
FIG. 16
FIG. 20
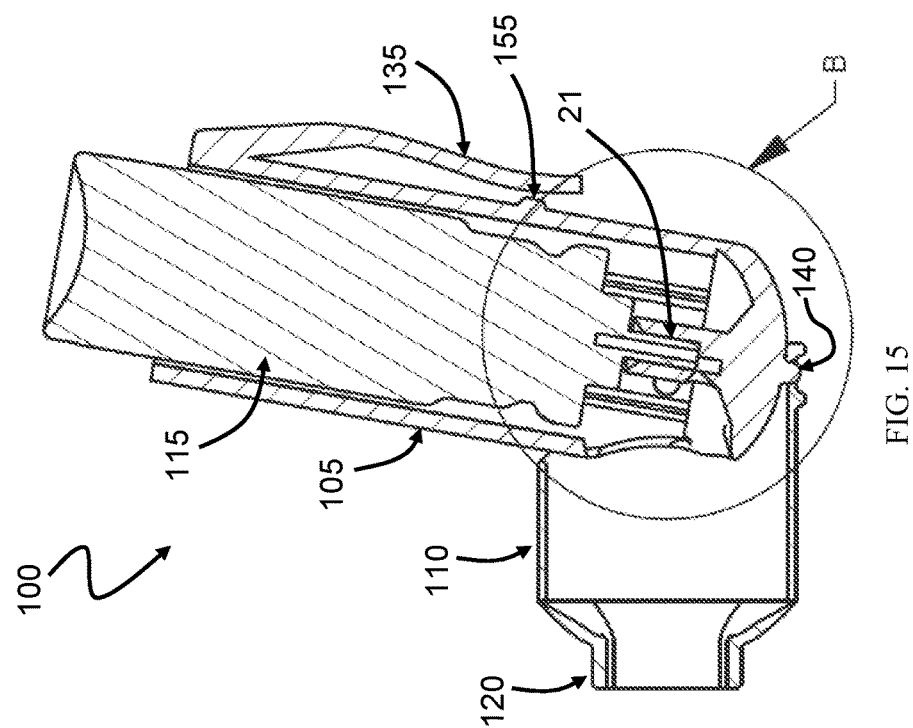
FIG. 15

INHALER HOUSING

TECHNICAL FIELD

The present invention relates to an inhaler housing. In particular, the present invention relates to a relatively compact inhaler housing.

BACKGROUND ART

An inhaler is a medical device for delivering medication into the body via the lungs. Inhalers have been used for many years in the treatment of diseases such as asthma, influenza or chronic obstructive pulmonary disease (COPD), which includes diseases such as chronic bronchitis and emphysema.

Typically, inhalers (also known as puffers or asthma pumps) comprise a pressurised canister of medication (including a propellant) attached to a plastic housing that includes an actuator. On actuation, the inhaler releases a metered dose of medication in aerosol form into the user's lungs through their mouth.

Conventional inhaler housings are typically relatively bulky, meaning that they can be difficult or awkward to carry in, for instance, a pocket or a small handbag. This can lead to a person electing not to carry their inhaler and potentially jeopardising their health if they experience an asthma attack (for example) while not carrying their inhaler.

Thus, there would be an advantage if it were possible to provide a inhaler that is relatively compact so as to be less bulky in order to encourage users to carry their inhaler with them more often It will be clearly understood that, if a prior art publication is referred to herein, this reference does not constitute an admission that the publication forms part of the common general knowledge in the art in Australia or in any other country.

SUMMARY OF INVENTION

The present invention is directed to an inhaler housing which may at least partially overcome at least one of the abovementioned disadvantages or provide the consumer with a useful or commercial choice.

With the foregoing in view, the present invention in one form, resides broadly in an inhaler housing comprising a receiving portion adapted to at least partially receive a container containing a medicament, and a dispensing portion through which the medicament is dispensed, wherein the receiving portion and the dispensing portion are movable relative to one another between a storage condition in which the receiving portion and the dispensing portion at least partially overlie one another and a use condition, wherein the dispensing portion and the receiving portion are configured to move between the storage condition and the use condition using both a sliding movement and a pivoting movement, and wherein the inhaler housing includes one or more retention members adapted to retain the inhaler housing in the use condition.

The receiving portion may be of any suitable size, shape or configuration. As previously stated, however, the receiving portion is adapted to at least partially receiving a container containing a medicament. Thus, in a preferred embodiment of the invention, the receiving portion may include an opening therein through which the container is received. The opening may be located in any suitable location on the receiving portion.

In some embodiments of the invention, the receiving portion may be substantially tubular. In this embodiment, the receiving portion may be of any cross-sectional shape, although it is preferred that the cross-sectional shape of the receiving portion may be substantially circular. Preferably, at least one end of the receiving portion may be open, and the open end of the receiving portion may form the opening through which the container is at least partially received.

In a preferred embodiment, the receiving portion may include a bore extending along at least a portion of its length. Preferably, the bore extends into the receiving portion from the open end thereof. It is envisaged that, in this embodiment of the invention, the container may be at least partially received within the bore.

The bore may be of any suitable diameter. However, in a preferred embodiment of the invention, the diameter of the bore is slightly larger than the diameter of the container. In this way, the container may be retained snugly within the receiving portion.

The bore may be provided with one or more retaining members. The retaining members may be of any suitable form, although in a preferred embodiment the retaining members may include one or more projections extending inwardly into the bore from an inner surface of the receiving portion. The one or more projections may include one or more ribs, fingers, lands, teeth or the like, or any suitable combination thereof. Preferably, when a container is received in the receiving portion, the one or more projections may be brought into abutment with an outer surface of the container, thereby assisting in retaining the container within the receiving portion through a frictional engagement.

In embodiments of the invention in which the projections comprise one or more ribs, the ribs may be oriented in any suitable manner. In a preferred embodiment, however, the one or more ribs may extend along the inner surface of the bore in a direction substantially parallel to the longitudinal axis of the bore, and therefore parallel to the longitudinal axis of the receiving portion.

The one or more projections may be spaced evenly around the inner surface of the bore, or may be disposed at random intervals. Preferably, the one or more projections are located substantially about the entire inner surface of the bore so as to enhance the frictional engagement between the projections and the container.

The receiving portion may be of any suitable length. For instance, the receiving portion may be at least as long as the container, such that the container may be entirely received within the receiving portion. More preferably, the receiving portion may be shorter in length than the container such that the container is only partially received within the receiving portion. In this way, a user may have ready access to a portion of the container, so as to remove the container from the receiving portion when empty, or to press the container to move it relative to the receiving portion in order to actuate the dispensing of the medicament from the container.

In some embodiments of the invention, the inhaler housing may include one or more connection members adapted to allow connection of the inhaler housing to an item. The item may be of any suitable form, and may include an item of clothing, a belt, bag or the like, or any suitable combination thereof. The connection members may be of any suitable form, and may include one or more straps, buckles, buttons, clasps, loops, ties, press studs, magnets hook and loop connectors, zips or the like. More preferably, the connection members may comprise one or more clips adapted to facilitate connection of the inhaler housing to the item. A connection member of the one or more connection members may be configured to retain the inhaler housing in the storage condition.

The connection members may be formed separately to the inhaler housing and may be adapted for fixed or temporary connection thereto. More preferably, however, the connection members may be integrally formed with the inhaler housing.

The connection members may be provided on the receiving portion, the dispensing portion or a combination of the two. Most preferably, the connection members may be located on the receiving portion.

The container may be of any suitable form, although it will be understood that the container may be largely conventional, comprising a pressurised metal canister containing a medicament and a propellant. The medicament may be used in the treatment of any suitable disease or disorder, although it is envisaged that the medicament may be typically used in the treatment of asthma, influenza or chronic obstructive pulmonary disease (COPD).

The receiving portion may further include an actuation portion adapted to assist in the dispensing of the medicament from the container. Any suitable actuation portion may be provided.

It is envisaged that the container may include a valve therein, through which the medicament exits the container. It is further envisaged that the container may include a valve stem extending outwardly from the container. Thus, in these embodiments of the invention, it is envisaged that the container may be received and retained in the receiving portion such that the valve stem is brought into abutment with, or close proximity to, the actuation portion. Preferably, further movement of the container relative to the receiving portion (typically by manual pressure applied to the container) may actuate the valve (by moving the container relative to the valve stem due to abutment of the valve stem with the actuation portion) so that medicament (and preferably a metered dose of medicament) may be released from the container.

In a preferred embodiment of the invention, the actuation portion may comprise an abutment portion against which the valve stem abuts such that, when further movement of the container relative to the receiving portion is actuated, the valve stem is unable to move relative to the receiving portion due to its abutments with the abutment portion. Instead, the container moves relative to the valve stem, thereby opening the valve and dispensing a quantity of medicament. The construction of the container is conventional, and no further description of this is required.

In some embodiments of the invention, the actuation portion may further comprise an expansion chamber into which medicament dispensed from the container may expand to form an aerosol. In some embodiments of the invention, the actuation portion may further comprise an outlet through which the medicament (for example, in aerosol form) may be directed to the user. Preferably, the outlet is located such that medicament may be directed towards the user's mouth. The outlet may be of any suitable form, although in some embodiments of the invention, the outlet may comprise a nozzle.

The outlet may be oriented in any suitable direction. For instance, the outlet may be oriented such that the medicament is dispensed through the outlet in a direction that is substantially co-axial with, or parallel to, a longitudinal axis of the receiving portion. Alternatively, the outlet may be oriented at an angle of less than 180° to the longitudinal axis of the receiving portion. For instance, the outlet may be oriented at an angle of between about 30° and about 150° to the longitudinal axis of the receiving portion. More preferably, the outlet may be oriented at an angle of between about 60° and about 120° to the longitudinal axis of the receiving portion. Most preferably, the outlet may be oriented at an angle of about 90° to the longitudinal axis of the receiving portion.

As previously stated, the receiving portion may comprise a first open end through which the container may be received within the receiving portion. An opposed second end of the receiving portion may also be open. More preferably, however, the opposed second end of the receiving portion may be substantially closed. In a preferred embodiment of the invention, the opening in the actuation portion may comprise the only opening in the second end of the receiving portion.

It is envisaged that the opposed second end of the receiving portion may be provided with a shaped portion. Any suitable shape of shaped portion may be provided, although it will be understood that the purpose of the shaped portion may be to abut, or be located in close proximity to, an inner surface of the dispensing portion when the inhaler housing is in the use condition. In this way, the presence of the shaped portion may reduce or eliminate the loss of medicament between the receiving portion and the dispensing portion. This is of particular importance when the medicament is delivered from a metered dose container. Any loss of medicament (by which it is meant, any medicament released from the container that does not reach the user for inhalation or ingestion) means that the user is receiving less than the required or desired dose of the medicament. This may lead to ineffective or insufficient treatment of the user's condition or alleviation or the user's symptoms.

The shaped portion of the receiving portion may be of any suitable shape. For instance, the shaped portion may be a truncated pyramid, cube, sphere, cone, cylinder or the like, or any suitable combination thereof. In one embodiment of the invention, the shaped portion may be substantially dome shaped.

In some embodiments of the invention, the shaped portion may be provided with one or more recesses, slots, grooves, openings or the like (or any combination thereof) therein. In this embodiment of the invention, it is envisaged that an inner surface of the dispensing portion may be provided with one or more projections (in the form of ribs, protrusions, teeth or the like, or a combination thereof) that are adapted to be received in the one or more recesses slots, grooves or openings in the shaped portion when the housing moves into the use condition. In this way, the housing may be retained in the use condition as required by the user. Preferably, the projections may be received in the recesses, slots, grooves or openings in such a manner that an audible signal (such as a click) is provided to the user to let the user know that the housing is in the use condition.

In an alternative embodiment of the invention, the shaped portion may be provided with the one or more projections, while the inner surface of the dispensing portion may be provided with the one or more recesses, slots, grooves or openings or the like.

In some embodiments of the invention, the outlet may be provided in a side wall of the receiving portion, such that, in the use condition, medicament exits the outlet into the dispensing portion. Alternatively, the outlet may be spaced inwardly from the side wall of the receiving portion. In this embodiment of the invention, the side wall of the receiving portion may be provided with an opening therein through which medicament exiting the outlet passes from the receiving portion to the dispensing portion.

The dispensing portion may be of any suitable size, shape or configuration. As previously stated, the dispensing portion and the receiving portion at least partially overlie one another in the storage condition. Thus, in embodiments of the invention in which the receiving portion comprises a tubular member, it is envisaged that the dispensing portion may also comprise a tubular member. Preferably, the dispensing portion may have the same, or a similar, cross-sectional shape to that of the receiving portion, at least along a portion of its length.

In some embodiments of the invention, the receiving portion may at least partially overlie the dispensing portion in the storage condition. Thus, in this embodiment of the invention, the dispensing portion may be at least partially received within the receiving portion in the storage condition.

Alternatively, the dispensing portion may at least partially overlie the receiving portion in the storage condition. In this embodiment, the receiving portion may be at least partially received within the dispensing portion in the storage condition. It is envisaged that, in this embodiment of the invention, the inner diameter of the tubular dispensing portion may be substantially equal to, or slightly larger than, the outside diameter of the tubular receiving portion. In this way, the receiving portion may be received relatively snugly within the dispensing portion. In this way, unwanted or accidental movement of the dispensing portion relative to the receiving portion may be reduced or eliminated.

The dispensing portion may move relative to the receiving portion between the storage condition and the use condition in any suitable manner. In a preferred embodiment of the invention, however, the dispensing portion may move relative to the receiving portion between the storage condition and the use condition in a sliding movement. Thus, in this embodiment of the invention, the receiving portion and the dispensing portion may move relative to one another in a telescoping action.

The sliding movement of the dispensing portion relative to the receiving portion may be achieved using any suitable technique. Preferably, however, the sliding movement of the dispensing portion relative to the receiving portion may be achieved manually by a user applying a force to the dispensing portion and/or the receiving portion in order to slidably move the dispensing portion relative to the receiving portion.

The dispensing portion may be adapted to move any distance relative to the receiving portion. More preferably, however, one or more movement limiting members may be provided to limit the distance the dispensing portion may slidably move relative to the receiving portion. Any suitable movement limiting members may be provided, such as one or more stop members (projections, ribs or the like) that define the limit of movement of the dispensing portion relative to the receiving portion.

In a preferred embodiment of the invention, one of the dispensing portion or the receiving portion may be provided with one or more recesses, channels, openings or the like, while the other of the dispensing portion of the receiving portion may be provided with one or more protrusions. In this embodiment of the invention, it is envisaged that, when the inhaler housing is assembled, the one or more protrusions may be located within the one or more recesses, channels, openings or the like.

It is envisaged that, as the dispensing portion and the receiving portion move between the storage condition and the use condition, the protrusions may move within the opening, recess or channel. However, the abutment of the protrusions against opposed ends of the channel, recess or opening may define the limit of movement of the dispensing portion relative to the receiving portion.

In a most preferred embodiment of the invention, the channel, recess or opening may be provide on the receiving portion, and, more specifically, in an outer surface of the receiving portion. The one or more protrusions may be provided on the dispensing portion, and, more specifically, on an inner surface of the dispensing portion.

The one or more recesses, channels or openings may be of any suitable size or shape, and may be located in any suitable orientation. Preferably, however, the one or more recesses, channels of openings may be oriented so as to be substantially parallel to the longitudinal axis of the receiving portion or substantially parallel to the longitudinal axis of the dispensing portion.

Any suitable number of channels, recesses or openings and protrusions may be provided. It is envisaged, however, that one protrusion may be located within each recess, channel or opening.

In a preferred embodiment of the invention, a pair of recesses, channels or openings may be provided. In this embodiment of the invention, the pair of recesses, channels or openings may preferably be provided on the receiving portion.

In a preferred embodiment of the invention, a pair of recesses, channels or openings may be provided on the receiving portion. The recesses, channels or openings may be provided on any suitable location and in any suitable orientation. Preferably, however, the pair of recesses, channels or openings may be spaced apart from one another about the circumference of the receiving portion. More preferably, the pair of recesses, channels or openings may be spaced apart from one another by approximately 180° about the circumference of the receiving portion.

As previously stated, the receiving portion and the dispensing portion may move relative to one another in a sliding movement between the storage condition and the use condition. In some embodiments of the invention, however, two movements may be required to move the receiving portion and the dispensing portion between the storage condition and the use condition.

The two movements may be of any suitable form. However, in a preferred embodiment of the invention, a first movement may be a sliding movement, while a second movement may be a pivoting movement. Preferably, from the storage condition, the receiving portion and the dispensing portion slide relative to one another, and then pivot relative to one another to move into the use condition. From the use condition, the dispensing portion and the receiving portion preferably pivot relative to one another and then slide relative to one another into the storage condition.

Pivotal movement of the dispensing portion relative to the receiving portion may occur at any suitable point following the sliding movement. In a preferred embodiment of the invention, however, the receiving portion and the dispensing portion may slide relative to one another to the limit of the sliding movement (for example, defined by the location of a stop member, or a protrusion within a channel, recess or opening) before the pivotal movement may occur.

The pivotal movement may occur about a pivot point. The pivot point may be of any suitable form, although in a preferred embodiment of the invention, the point about which the dispensing portion pivots relative to the receiving portion may be the stop member of the protrusion located within the channel, recess or opening.

The dispensing portion and the receiving portion may pivot any suitable distance relative to one another. It is envisaged, however, that when the inhaler housing is in the use condition, the dispensing portion and the receiving portion may be oriented at an angle of between about 60° and about 130° to one another. More preferably, in the use condition the dispensing portion and the receiving portion may be oriented at an angle of between about 70° and about 120° to one another. Yet more preferably, in the use condition the dispensing portion and the receiving portion may be oriented at an angle of between about 80° and about 110° to one another. Most preferably, in the use condition the dispensing portion and the receiving portion may be oriented at an angle of about 100° to one another.

As the dispensing portion pivots relative to the receiving portion into the use condition, a user may be provided with an indication that the inhaler housing has moved into the use condition. For instance, the dispensing portion and/or the receiving portion may be provided with one or more retention members adapted to retain the dispensing portion and the receiving portion in the use condition. Any suitable retention members may be provided, such as one or more catches, clasps, detents or the like, or any suitable combination thereof. It is envisaged that the retention members may engage or connect in a manner that indicates to the user that the inhaler housing is in the use condition. For instance, the retention members may engage or connect with an audible sound (such as a click or the like) to indicate that the inhaler housing is in the use condition. The one or more retention members may comprise a nipple and a corresponding aperture which engage with each other in an interference fit.

Alternatively, the inhaler housing may be retained in the use condition via a frictional engagement between the receiving portion and the dispensing portion.

In one embodiment of the invention, the recess may be provided with a retention portion at an end thereof. Preferably, the retention portion may be provided at the end of the channel at which pivotal movement of the receiving portion relative to the dispensing portion is possible. Any suitable retention portion may be provided, although in this embodiment of the invention, the retention member may comprise an extension of the recess. It is envisaged that, as the receiving portion and the dispensing portion pivot relative to one another, the protrusion may move into the extension, thereby retaining or locking the inhaler housing in the use condition. The protrusion may simply move into the extension as the dispensing portion pivots relative to the receiving portion, or further sliding movement of the dispensing portion relative to the receiving portion following the pivotal movement may be required to move the protrusion into the extension. The extension may be located at any suitable orientation relative to the recess. In a preferred embodiment of the invention, however, the extension is oriented at an angle to the recess. For instance, the extension may be oriented at an angle of between about 30° and about 150° to the longitudinal axis of the recess. More preferably, the extension may be oriented at an angle of between about 60° and about 120° to the longitudinal axis of the recess. Most preferably, the extension may be oriented at an angle of about 90° to the longitudinal axis of the recess.

It is envisaged that the inhaler housing may be moved out of the use condition through the application of a force (and particularly a manual force applied by the user) to the housing, thereby moving the protrusion out of its retention within the extension.

In some embodiments of the invention, the dispensing portion and/or the receiving portion may be provided with one or more cut-out portions. The cut-out portions may be of any suitable size, shape or configuration, although preferably, the cut-out portions extend inwardly into the dispensing portion and/or the receiving portion from an end thereof.

Most preferably, the one or more cut-out portions may be provided in the dispensing portion. In this embodiment, it is envisaged that, in the use condition, a portion of the receiving portion may be received in the cut-out portion. Preferably, the cut-out portion is sized so that at least an outer surface of the receiving portion may be located in abutment with, or close proximity to, at least a portion of an edge of the cut-out portion in the use condition. In some embodiments of the invention, the abutment of the receiving portion with an edge of the cut-out portion may define the limit of pivotal movement of the receiving portion relative to the dispensing portion.

As previously stated, the dispensing portion may be substantially tubular. At least one end of the dispensing portion may be an open end, although in a preferred embodiment of the invention, both opposed ends of the dispensing portion may be open ends. In this embodiment of the invention, it is envisaged that medicament exiting the receiving portion may enter the dispensing portion through a first open end thereof. The medicament may then exit the dispensing portion (at which point it may be inhaled or ingested by the user) through an opposed second open end of the dispensing portion.

The second open end of the dispensing portion (through which medicament exits the inhaler housing) may be of any suitable form. In some embodiments of the invention, the second open end may have the same diameter as the remainder of the dispensing portion. In an alternative embodiment of the invention, the second open end of the dispensing portion may be provided with a shaped portion. The shaped portion may be provided so that, for instance, a user may more comfortably place their mouth about the shaped portion. Alternatively, the shaped portion may be provided so that the shaped portion may be connected to another item, such as a spacer or the like. In this embodiment of the invention, the shaped portion may be shaped so as to facilitate connection to a spacer.

In some embodiments of the invention the second open end of the dispensing portion may be provided with a cover member. Any suitable cover member may be provided, such as, but no limited to, a cap or plug. The cover member may be of any suitable size, shape or configuration, although it is envisaged that the cover member may be adapted to be retained on the open second end of the dispensing portion (or the shaped portion, if present) when the inhaler housing is not in use.

Preferably, the cover member is adapted to be located over the open end of the dispensing portion and extend at least partway along a sidewall of the dispensing portion. Thus, in this embodiment of the invention, the cover member may comprise a cap. Preferably, the cap comprises a base wall and one or more sidewalls extending therefrom, the one or more sidewalls extending along the sidewall of the dispensing portion. The cap may be retained on the dispensing portion using any suitable technique. For instance, the cap may be retained on the dispensing portion via a frictional engagement. Alternatively, the cap and the dispensing portion may be provided with one or more connection members adapted to connect the cap to (and retain the cap on) the dispensing portion. Any suitable connection members may be provided, such as one or more clamps, clasps, pins, or the like. Alternatively, the cap may be adapted for retention on the dispensing portion via a screw-threaded engagement between the cap and the dispensing portion.

In one embodiment of the invention, dispensing portion or the cap may be provided with a groove or channel extending at least partway about the outer circumference of the dispensing portion or the inner surface of the cap, and specifically on the inner surface of the sidewall of the cap. The other of the dispensing portion or the cap may be provided with a projection (in the form of a lip or the like) adapted to engage with, and be retained in, the groove or channel in order to retain the cap on the dispensing portion.

In a most preferred embodiment, the dispensing portion may be provided with the groove or recess while the cap may be provided with the lip.

The inhaler housing may be fabricated from any suitable material. For instance, the inhaler housing may be fabricated from metal, glass, a polymeric substance, fibreglass or the like. In a preferred embodiment of the invention, the inhaler housing may be fabricated from one or more types of polymeric substance, such as a plastic. In particular, the inhaler housing may be fabricated from polyethylene terephthalate (PET or PETE), high-density polyethylene (HDPE), polyvinyl chloride (PVC), low-density polyethylene (LDPE), polypropylene (PP), polystyrene (PS), or the like, or any suitable combination thereof.

The inhaler housing may be fabricated from any suitable technique. Preferably, however, the housing may be fabricated using a moulding technique. The inhaler housing may be moulded in a single piece or may be moulded in two or more pieces that are adapted for fixed or temporary connection to one another.

It is envisaged that medicament containers or canisters may be provided in a variety of different sizes (both in terms of length and diameter), and may contain a variety of different doses of the medicament. As a result, it is envisaged that the inhaler housing of the present invention may be fabricated in a number of different sizes so as to accommodate canisters of different sizes. It is envisaged that, for all canister sizes, the canister will be retained snugly in a frictional engagement within the receiving portion. Thus, it is envisaged that the diameter and/or length of receiving portion and/or the dispensing portion may be varied so as to snugly accommodate a canister of any size. In this way, the inhaler housing of the present invention may be made more compact and therefore easier to carry and less likely to be left behind when exercising, using a small bag (such as a small handbag) or wearing clothing where a conventional inhaler may be too bulky to comfortably carry in a pocket or the like.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 4 illustrates a side view of an inhaler housing according to an embodiment of the present invention.

FIG. 5 illustrates a plan view of an inhaler housing according to an embodiment of the present invention.

FIG. 6 illustrates a side view of an inhaler housing according to an embodiment of the present invention.

FIG. 15 illustrates a cross-sectional view of the inhaler housing through A-A of FIG. 14, in the use condition.

FIG. 16 illustrates an enlarged cross-sectional view of portion B of the inhaler housing of FIG. 15.

FIG. 20 illustrates an end view of the of the inhaler housing of FIG. 12, in a storage condition.

DESCRIPTION OF EMBODIMENTS

Figure 1:
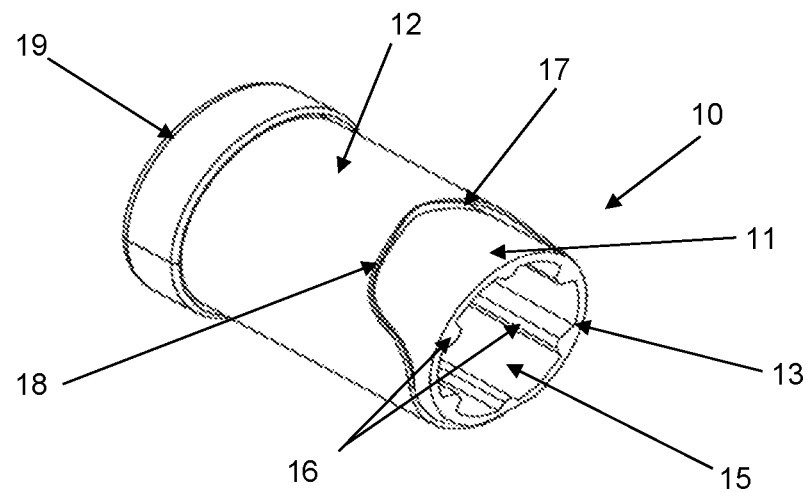
FIGS. 1 and 2 illustrate isometric views of an inhaler housing according to an embodiment of the present invention.
Figure 2:
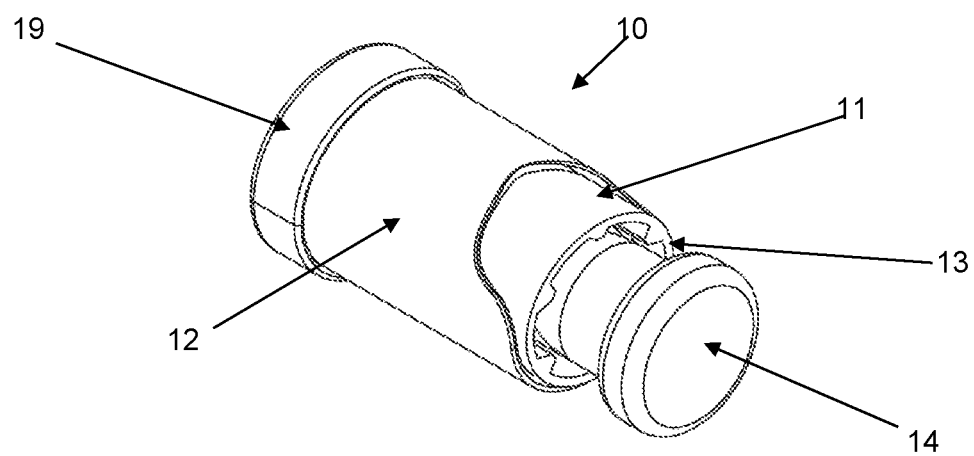

In FIGS. 1 and 2 there are illustrated isometric views of an inhaler housing 10 according to an embodiment of the present invention. The housing 10 is shown in the storage condition in which a receiving portion 11 is partly received within a dispensing portion 12.

Both the receiving portion 11 and the dispensing portion 12 are substantially tubular, with the dispensing portion 12 having a slightly large diameter than the receiving portion 11 such that the dispensing portion partially overlies the receiving portion in the storage condition.

A first end 13 of the receiving portion 11 is open so as to receive a container in the form of a pressurised canister 14 (shown in FIG. 2). The canister 14 contains a medicament to be dispensed through the inhaler housing 10.

The inner surface 15 of the receiving portion 11 is provided with a plurality of ribs 16 that are adapted to provide a frictional engagement between the ribs 16 and the canister 14, thereby preventing unwanted or accidental removal of the canister 14 from the housing 10.

The dispensing portion 12 is provided with a cut out portion 17 in an outer surface thereof. When the inhaler housing is in the use condition, a portion of the outer surface of the receiving portion 11 is received in the cut out portion 17, such that the outer surface abuts (or is retained in close proximity to) the edge 18 of the dispensing portion 12 in the region of the cut out portion 15.

In the embodiments of the invention shown in FIGS. 1 and 2, an end of the dispensing portion 12 is provided with a cap 19 that covers an open end (obscured) of the dispensing portion 12 and extends along a portion of the sidewall of the dispensing portion 12. The cap 19 prevents contamination of the open end (obscured) of the dispensing portion 12 (over which a user will typically place their mouth) and also ensures that, if the medicament is accidentally discharged, the medicament will be retained in the housing 10, instead of in a user's pocket, handbag or the like. The skilled addressee will readily appreciate that other types of caps and/or covers may be used to provide a similar function, including a cap that engages with an inside of the open end (much like a plug).

Figure 3:
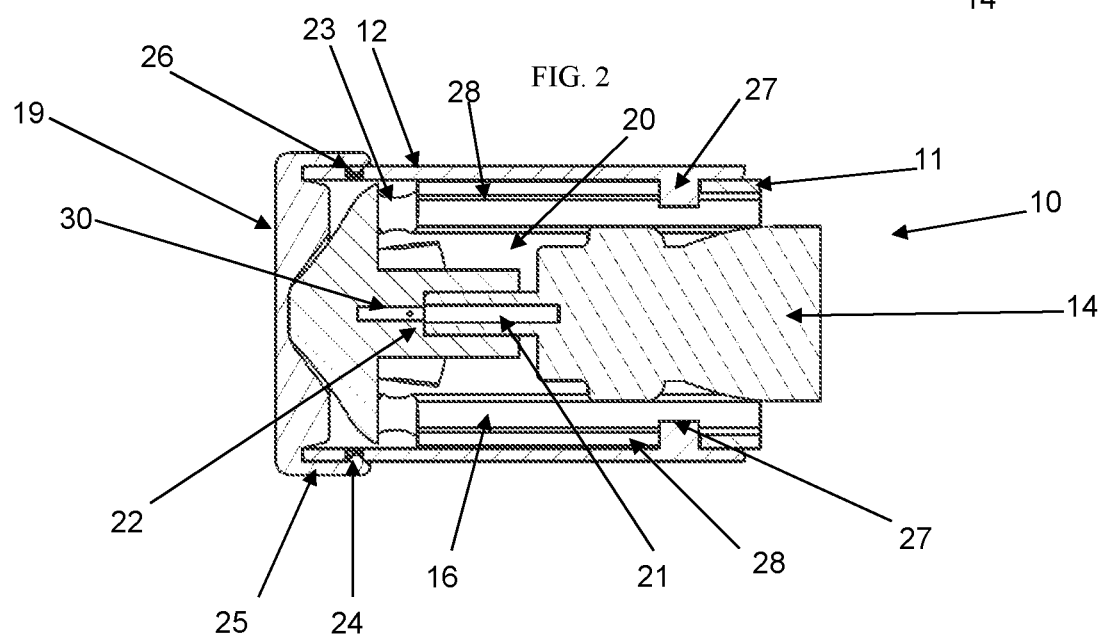
FIG. 3 illustrates a cross-sectional view of an inhaler housing according to an embodiment of the present invention.

In FIG. 3, a cross-sectional view of the inhaler housing 10 of FIG. 2 is illustrated. In this Figure it may be seen that the dispensing portion 12 overlies a portion of the receiving portion 11 when in the storage condition. The canister 14 is received in the receiving portion 11 and is retained therein in a frictional engagement with ribs 16 located in the bore 20 of the tubular receiving portion 11.

The canister 14 includes a valve stem 21 that extends outwardly from the canister 14 and abuts an actuation portion 30 that includes an abutment surface 22. Further movement of the canister 14 relative to the housing 11 also results in movement of the canister 14 relative to the valve stem 21, thereby actuating a valve and dispensing medicament from the canister 14. The medicament exist the receiving portion 11 through an opening 23 in a sidewall thereof. When the inhaler housing 10 is in the use condition, the medicament exiting through the opening 23 enters the dispensing portion 12 and exits the housing through the end of the dispensing portion 12 on which the cap 19 is located in FIG. 3.

The cap 19 is provided with ribs 24 that extend partway about an inner surface of a sidewall 25 of the cap 19. The ribs 24 are received in grooves 26 that extend partway about the outer surface of the dispensing portion 12. In this way, the cap 19 is retained on the inhaler housing 10 and the risk of unwanted or accidental removal of the cap 19 is reduced or eliminated.

In FIG. 3 it may be seen that the inner surface of the dispensing portion 12 is provided with a pair of protrusions 27. The protrusions 27 are received within channels 28 in the outer surface of the receiving portion 11. As the inhaler housing 10 moves between the storage condition and the use condition, the dispensing portion 12 and the receiving portion 11 initially slide relative to one another. The limit of sliding movement of the dispensing portion 12 relative to the receiving portion 11 is defined by the abutment of the protrusions 27 against opposite ends of the channel 28.

FIG. 4 illustrates a side view of an inhaler housing 10 according to an embodiment of the present invention. In this Figure, the inhaler housing 10 is in the use condition in which medicament may be dispensed to a user.

To move the housing 10 from the storage condition shown in FIGS. 1 to 3 to the use condition shown in FIG. 4, the dispensing portion 12 and the receiving portion 11 are first moved in a sliding motion relative to one another. The dispensing portion 12 and the receiving portion 11 slide relative to one another until the protrusion (obscured) on the inner surface of the dispensing portion 12 abuts the end of the channel 28 in the sidewall of the receiving portion 11. At this point, the receiving portion 11 and the dispensing portion 12 are pivoted relative to one another into the use condition shown in FIG. 4.

The point about which the receiving portion 11 and the dispensing portion pivot relative to one another is the location of the protrusion (obscured) located in the channel 28. The limit of pivotal movement of the dispensing portion 12 relative to the receiving portion 11 is defined by the point at which the wall of the receiving portion 11 abuts the edge 18 of the cut out portion 17 of the dispensing portion 12.

In the use condition, the receiving portion 11 and the dispensing portion 12 are oriented relative to one another such that the included angle between the receiving portion 11 and the dispensing portion 12 is about 100°.

In the use condition illustrated in FIG. 4, a medicament is dispensed to the user by applying a force to the canister 14 in a direction whereby the canister 14 is pushed further into the receiving portion 11. This movement of the canister 14 relative to the receiving portion 11 actuates the valve (obscured) thereby releasing a medicament into the actuation portion (obscured) of the receiving portion 11. Typically, the medicament forms an aerosol in the actuation portion (obscured) and is directed from the receiving portion 11 into the dispensing portion 12.

Typically a user will place their mouth over the open end 31 of the dispensing portion 12 so that medicament that enters the dispensing portion 12 from the receiving portion 11 exits the dispensing portion 12 through the open end 31 and into the user's mouth where it is inhaled or ingested.

FIG. 5 illustrates a plan view of an inhaler housing 10 according to an embodiment of the present invention. The inhaler housing 10 of FIG. 5 is the same as that shown in FIG. 4.

In FIG. 5, the frictional engagement between the canister and the ribs 16 on the inner surface 15 of the receiving portion 11 may be more clearly seen. In addition, the abutment between the receiving portion 11 and the edge 18 of the cut out portion 17 of the dispensing portion 12 when the inhaler is in the use condition may be more clearly seen.

Further, the groove 26 in the dispensing portion 12 may be seen in this Figure. The groove 26 is provided so that a rib (not shown) on the cap (not shown) may be retained therewithin, thereby reducing or eliminating the possibility of unwanted or accidental removal of the cap (not shown) from the dispensing portion 12.

FIG. 6 illustrates a side view of an inhaler housing 10 according to an embodiment of the present invention. The inhaler housing 10 of FIG. 6 is essentially identical to that of FIG. 4 with the exception that the inhaler housing illustrated in FIG. 6 includes a clip 29 that allows the inhaler housing 10 to be retained on a user's belt, clothing, bag or the like.

Figure 7:
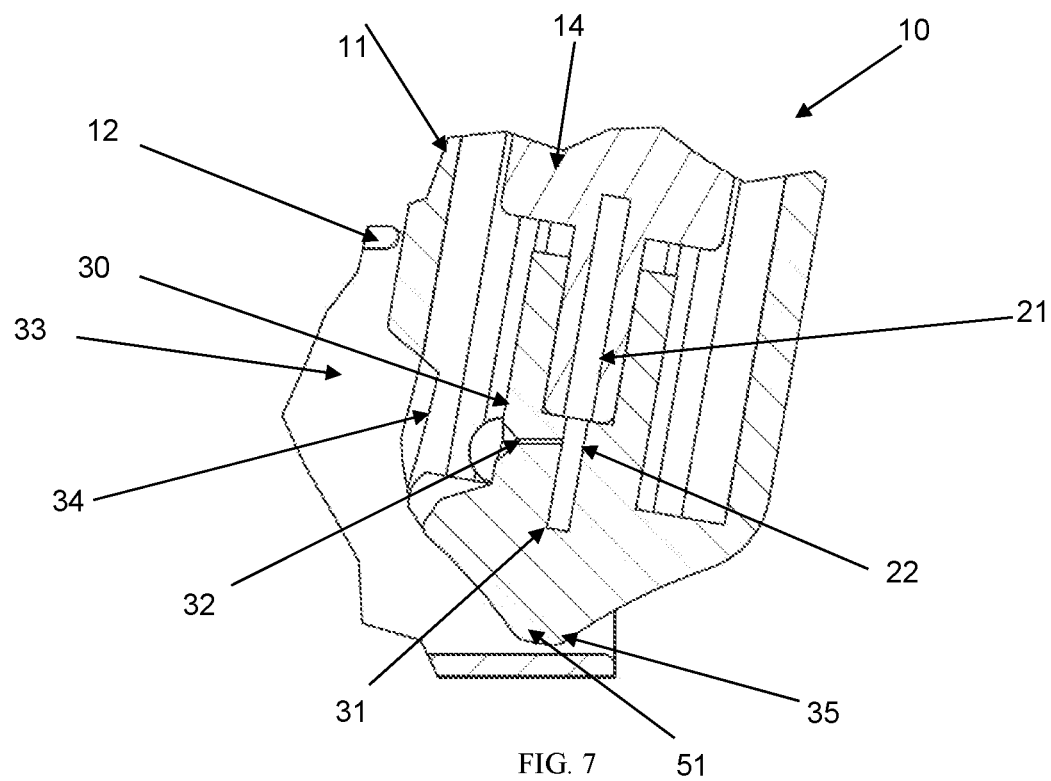
FIG. 7 illustrates a cross-sectional view of an inhaler housing according to an embodiment of the present invention.

FIG. 7 illustrates a cross-sectional view of an inhaler housing 10 according to an embodiment of the present invention. In this Figure, the inhaler housing 10 is in the use condition, as illustrated in FIGS. 4 to 6.

The function of the actuation portion 30 of the housing 10 may be more clearly seen in this Figure. The valve stem 21 of the canister 14 is located in abutment with the abutment portion, such that movement of the canister 14 further into the receiving portion 11 (typically achieved by applying a manual force to the end of the canister 14) results in movement of the valve stem 21 relative to the canister 14. This in turn actuates the valve (not shown) in the canister 14, dispensing medicament through the valve stem 21 into the actuation portion 30.

The actuation portion 30 is provided with an expansion chamber 31 which medicament exiting the canister 14 enters and expands to form an aerosol. The aerosol then exits the actuation portion 30 through an outlet 32 in the actuation portion 30 and an opening 34 in the sidewall of the receiving portion 11 and enters the bore 33 within the dispensing portion 12. The medicament then exits the dispensing portion 12 where it is inhaled or ingested by a user.

It will be noted in FIG. 7 that the end 35 of the receiving portion 11 adjacent the actuation portion is a closed end. In this way, medicament exiting the receiving portion 11 is directed through the opening 34, and cannot exit the receiving portion 11 in any other direction. This is important when the canister 14 provided a metered dose of medicament, as any medicament not directed through the opening 34 would not reach the user, meaning that the user would not receive the required does of medicament.

It will also be noted that the end 35 of the receiving portion 11 adjacent the actuation portion 11 is substantially dome shaped. By providing such a shaped portion 51 on the end 35 of the receiving portion 11, a gap between the end 35 and the inner surface of the dispensing portion 12 may be reduced or eliminated, thereby reducing or eliminating the risk of the loss of medicament between the end 35 and the dispensing portion 12.

Figure 8:
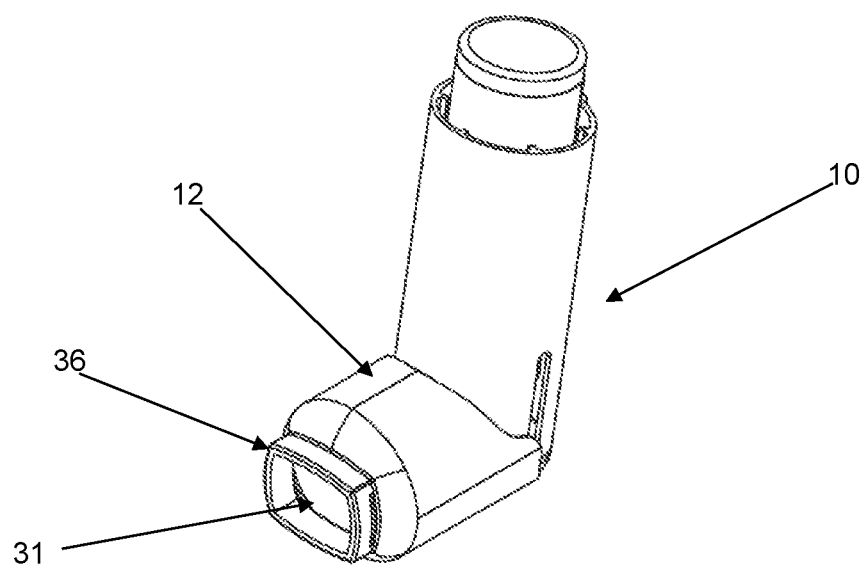
FIG. 8 illustrates an isometric view of an inhaler housing according to an embodiment of the present invention.

FIG. 8 illustrates an isometric view of an inhaler housing 10 according to an embodiment of the present invention. The inhaler housing 10 is essentially the same as that shown in FIG. 4, with the exception that the open end 31 of the dispensing portion 12 is provided with a shaped portion 36. The shaped portion 36 is shaped so as to facilitate connection of the dispensing portion 12 to another item, such as a spacer (not shown).

Figure 9:
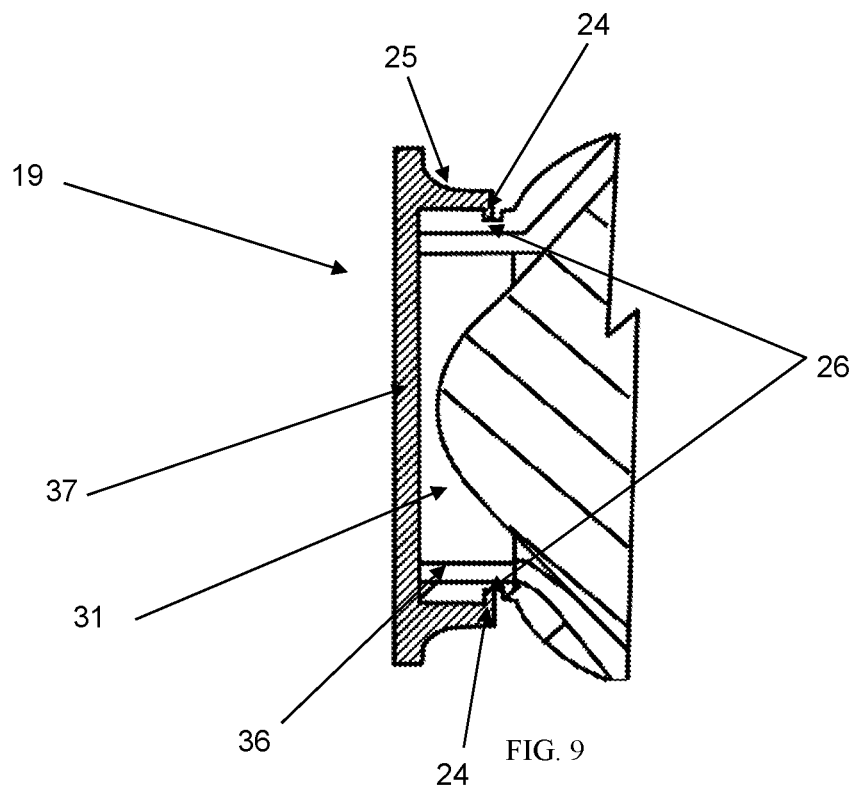
FIG. 9 illustrates a cross-sectional view of an inhaler housing according to an embodiment of the present invention.

FIG. 9 illustrates a cross-sectional view of an inhaler housing 10 according to an embodiment of the present invention. The inhaler housing 10 illustrated in FIG. 9 is that of FIG. 8, with the addition of a cap 19.

The cap 19 includes a cover member 37 that covers the open end 31 of the dispensing portion 12. The cap 19 also includes an annular sidewall 25 that extends along an outer surface of the shaped portion 36. The inner surface of the sidewall 25 is provided with ribs 24 that are received in grooves 26 that extend partway about the outer surface of the shaped portion 36. In this way, the cap 19 is retained on the inhaler housing 10 and the risk of unwanted or accidental removal of the cap 19 is reduced or eliminated.

Figure 10:
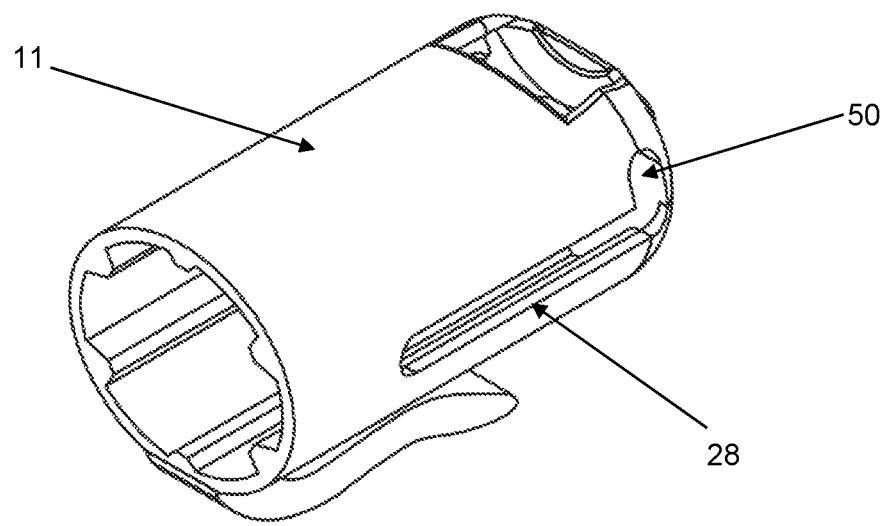
FIG. 10 illustrates an isometric view of an inhaler housing according to an embodiment of the present invention.

FIG. 10 illustrates an isometric view of an inhaler housing according to an embodiment of the present invention. Specifically, FIG. 10 illustrates an isometric view of a receiving portion 11 according to an embodiment of the present invention.

In this Figure, a channel 28 is provided in the sidewall of the receiving portion 11. The protrusion (not shown) on the inner surface of the dispensing portion (not shown) slides within the channel 28 in order to move the receiving portion 11 and the dispensing portion (not shown) between the storage and use conditions.

In FIG. 10, the channel 28 is provided with an extension 50. The extension 50 is oriented at approximately 90° to the channel 28 such that, as the dispensing portion (not shown) pivots relative to the receiving portion 11, the protrusion (not shown) on the inner surface of the dispensing portion (not shown) moves into the extension 50, thereby retaining the housing in the use condition.

Figure 11:
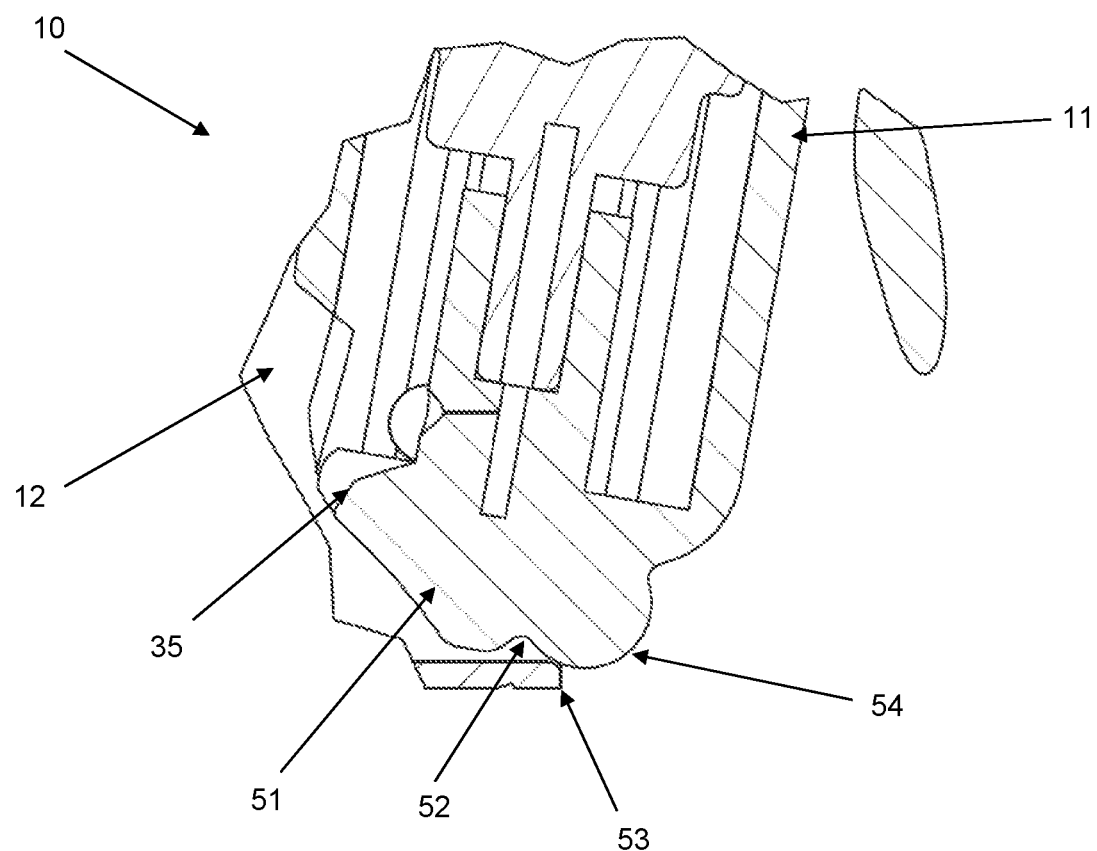
FIG. 11 illustrates a cross-sectional view of an inhaler housing according to an embodiment of the present invention.

In FIG. 11 there is illustrated a cross-sectional view of an inhaler housing 10 according to an embodiment of the present invention. In this Figure, the shaped portion 51 at the closed end 35 of the receiving portion 11 is provided with a groove 52 therein. The groove 52 is adapted to receive an edge 53 of the dispensing portion 12 therein when the housing 10 is in the use condition.

It is envisaged that, as the edge 53 of the dispensing portion 12 enters the groove 52, an audible snap or click may be emitted, thereby indicating to the user that the housing 10 is in the use condition. In addition, the reception of the edge 53 in the groove 52 reduces or eliminates the accidental or unwanted movement of the housing 10 out of the use condition.

The shaped portion 51 of the receiving portion 11 is also provided with an enlarged portion 54 adapted to further reduce or eliminate the accidental or unwanted movement of the housing 10 out of the use condition.

Figure 12:
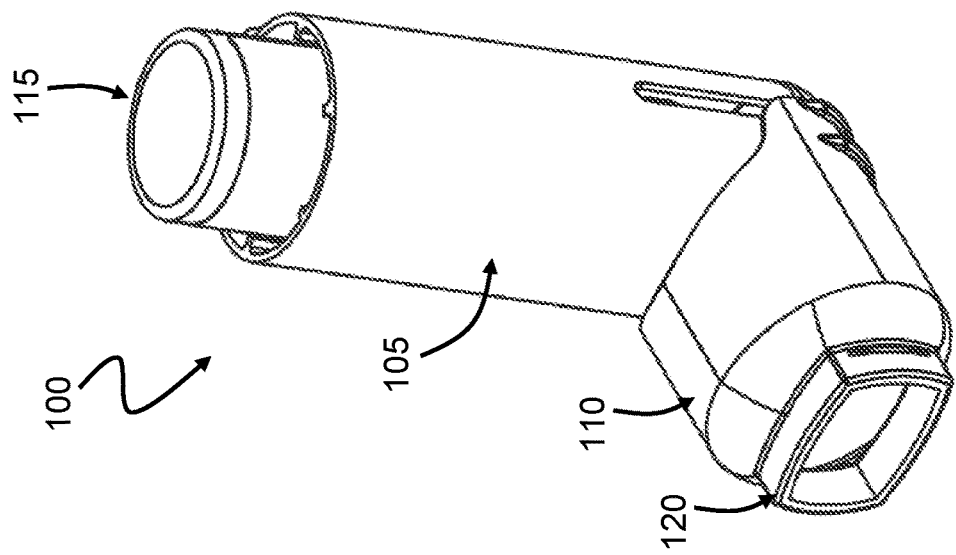
FIG. 12 illustrates an isometric view of an inhaler housing in a use condition, according to an alternative embodiment of the present invention.

FIG. 12 illustrates an isometric view of an inhaler housing 100, according to an alternative embodiment of the present invention. The housing 100 is similar to the housing 10 and can move between a use condition, in which medicament may be dispensed to a user, and a storage condition.

In particular, the housing 100 includes a receiving portion 105 and the dispensing portion 110, both of which are substantially tubular and are configured to pivot and slide relative to each other, as outlined below. The receiving portion 105 includes a container in the form of a pressurised canister 115 therein, and the dispensing portion 110 includes a shaped mouthpiece portion 120, which is shaped so as to facilitate connection of the dispensing portion 110 to another item, such as a spacer (not shown), or be used directly by a patient.

An inner surface of the dispensing portion 110 is provided with a pair of protrusions (much like the protrusions of the dispensing portion 12) which are received within channels 125 in the receiving portion 105. The protrusions on the inner surface of the dispensing portion 110 slide within the channel 125 in order to move the receiving portion 105 and the dispensing portion 110 between the storage and use conditions.

The channels 125 include extensions (obstructed by the dispensing portion 110), similar to the extension 50, which are oriented at approximately 90° to the channels 125 such that, as the dispensing portion 110 pivots relative to the receiving portion 105, the protrusions moves into the extension, thereby retaining the housing 100 in the use condition.

Figure 13:
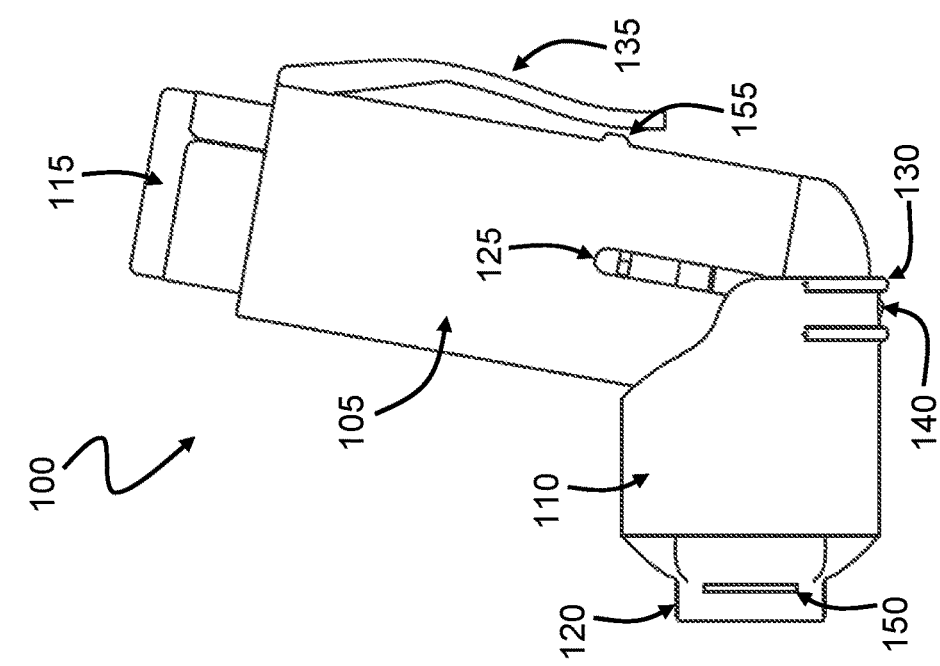
FIG. 13 illustrates a side view of the inhaler housing of FIG. 12, in the use condition.

As best illustrated in FIG. 13, a lower portion of the dispensing portion 110 includes support ribs 130, configured to provide strength and rigidity to the dispensing portion 110, particularly when a force is applied to the canister 115 in use. As such, the ribs 130 may prevent deformation of the dispensing portion 110 when pressure is applied to an underside thereof. The housing 100 further includes a clip 135, on the receiving portion 105 that allows the inhaler housing 10 to be retained on a user's belt, clothing, bag or the like, much like the clip 29.

As best illustrated in FIG. 15, a lower end of the receiving portion 105 includes a retention member in the form of a nipple 140, which extends into, and locks into a corresponding retaining aperture of the dispensing portion 110 in a press-fit (interference fit) arrangement. The nipple 140, when locked into the retaining aperture, prevents the receiving portion 105 from pivoting relative to the dispensing portion 110, and thus further holds the housing in the use condition.

The retaining aperture is located between first and second ribs 130. As such, any weakness in the dispensing portion 110 caused by the aperture is compensated for by the ribs 130. This is particularly useful as the aperture is located at a position where the user will hold (and press on) the housing 100.

Figure 14:
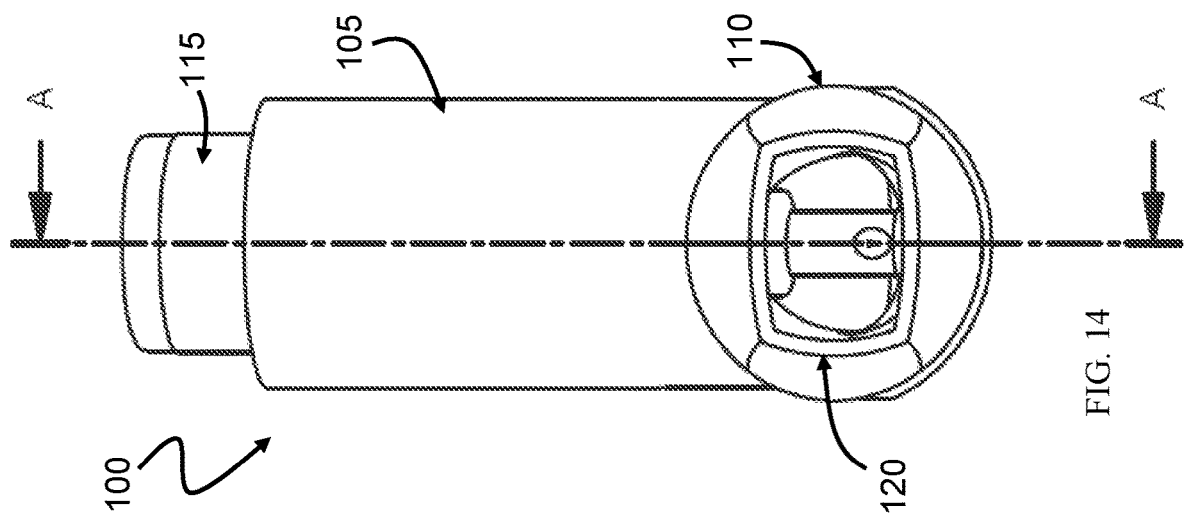
FIG. 14 illustrates a front view of the inhaler housing of FIG. 12, in the use condition.

In FIG. 15, a cross-sectional view of the inhaler housing 100 along A-A of FIG. 14 is illustrated. The canister 115 includes a valve stem 21 that extends outwardly from the canister 14 and abuts an actuation portion 30, in the same manner as the housing 10. As such, movement of the canister 115 relative to the housing 100 actuates a valve causing dispensing of a medicament from the canister 115. The medicament exits the housing through the mouthpiece 120.

Figure 17:
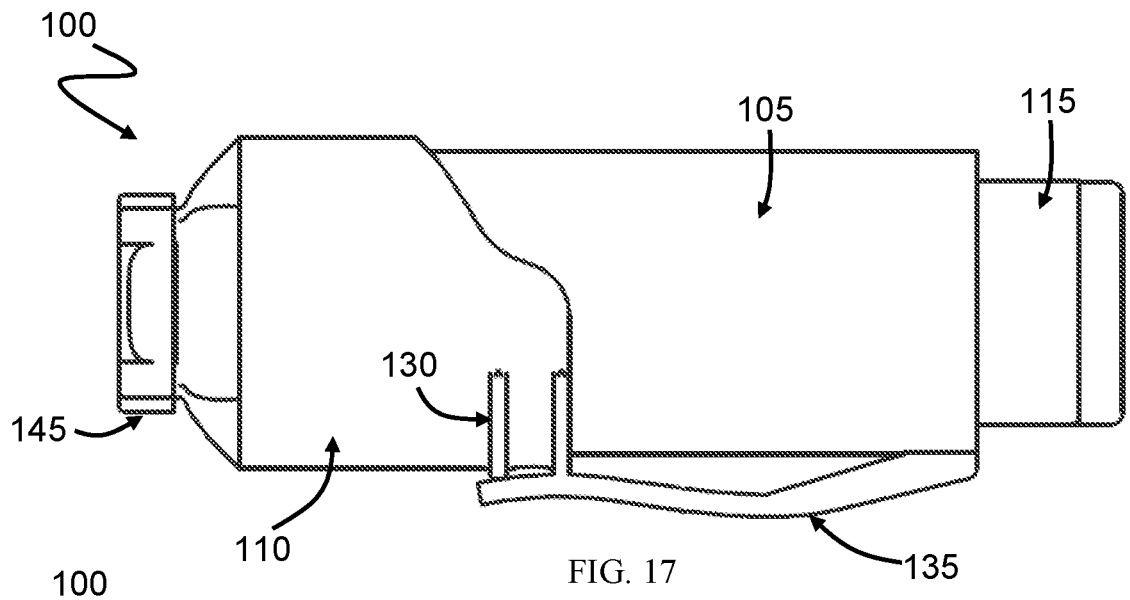
FIG. 17 illustrates a side view of the inhaler housing of FIG. 12, in a storage condition.
Figure 18:
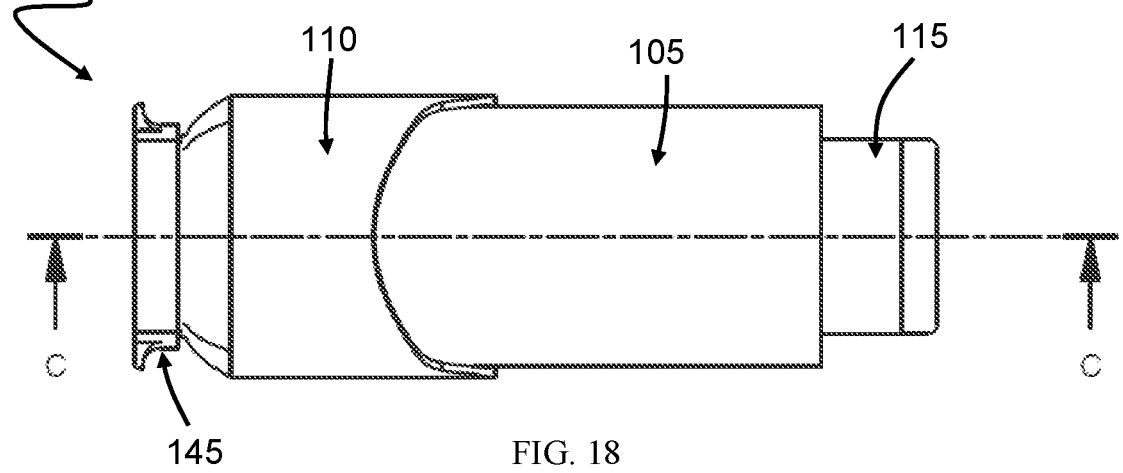
FIG. 18 illustrates a top view of the inhaler housing of FIG. 12, in a storage condition.
Figure 19:
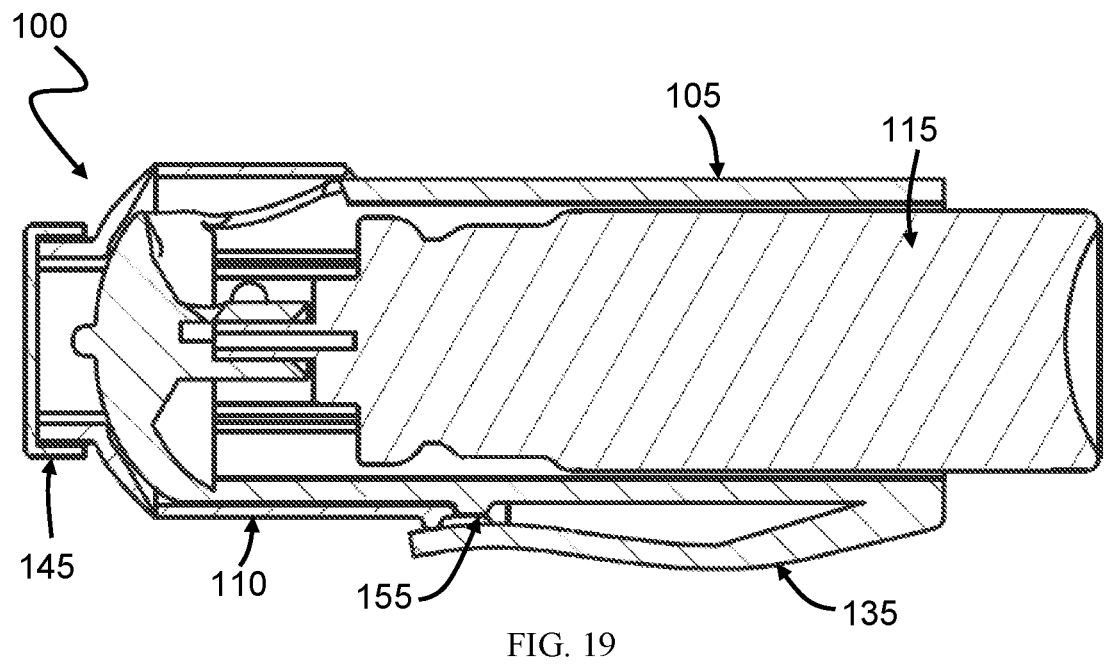
FIG. 19 illustrates a cross-sectional view of the inhaler housing through C-C of FIG. 18, in the storage condition.

To move the housing 100 from the use condition to the storage condition, force is applied to the dispensing portion 110 and the receiving portion 105 in a pivotal direction until the nipple leaves the retaining aperture, enabling the protrusions (obscured) to leave the extensions and enter the channels. At this point, an axis of the dispensing portion 110 and an axis of the receiving portion 105 become aligned, and may slide relative to each other such that an end of the receiving portion 105 is received within the dispensing portion 110, as illustrated in FIG. 17. In particular, the dispensing portion 110 has a slightly large diameter than the receiving portion 105 such that the dispensing portion 110 partially overlies the receiving portion 105 in the storage condition.

In the storage condition, a retention member in the form of a second nipple 155, which is located on a sidewall of the receiving portion 105 adjacent to the clip 135, extends into, and locks into the retaining aperture of the dispensing portion 110 in a press-fit (interference fit) arrangement. The nipple 155, when locked into the retaining aperture, prevents the receiving portion 105 from sliding relative to the dispensing portion 110, and thus further holds the housing in the storage condition. This is particularly useful in that it prevents the housing 100 from inadvertently sliding open when held in a pocket or purse, for example.

The shaped mouthpiece portion 120 is provided with a cap 145 that covers the mouthpiece portion 120, and prevents dust, dirt or debris from entering the mouthpiece portion 120. The cap 145 is provided with ribs (obscured) that that are received in grooves 150 of the mouthpiece portion to engage with the cap 145 and retain the cap 145 thereon.

As best illustrated in FIG. 20, the dispensing portion 110 is oval in cross-section, as a width 110a of the dispensing portion 110 is larger than a height 110b of the dispensing portion 110. This prevents the housing 100 from rolling around when in the storage condition.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

What is claimed is:

1. An inhaler housing, comprising:
   a receiving portion adapted to at least partially receive a container containing a medicament, the receiving portion including a plurality of retention members; and
   a dispensing portion through which the medicament is dispensed, the dispensing portion including a mouthpiece through which the medicament exits the inhaler housing, and an opening for receiving the receiving portion;
   wherein the receiving portion and the dispensing portion are movable relative to one another between a storage condition and a use condition, in which the receiving portion and the dispensing portion at least partially overlie one another;
   wherein the dispensing portion and the receiving portion are configured to move between the storage condition and the use condition using both a sliding movement and a pivoting movement;
   wherein a first protrusion of the plurality of retention members is located at a lower end of the receiving portion and holds the inhaler housing in the use condition;
   wherein a second protrusion of the plurality of retention members is located at a sidewall of the receiving portion and holds the inhaler housing in the storage condition;
   wherein the receiving portion defines at least one channel along which the
   dispensing portion is configured to move between the storage condition and the use condition, wherein the at least one channel defines an extension at an end thereof, the extension being oriented at an angle to the at least one channel, wherein the extension is adapted to receive a protrusion of at least one protrusion of the dispensing portion in order to further hold the inhaler housing in the use condition; and
   wherein the dispensing portion further includes a retaining aperture, wherein the retaining aperture is configured to receive the first protrusion in the use condition and receive the second protrusion in the storage condition.

2. The inhaler housing according to claim 1, wherein the plurality of retention members hold the inhaler housing in the use condition and the storage condition by interference fit.

3. The inhaler housing according to claim 1, wherein the lower end of the receiving portion seals the dispensing portion from inside the mouthpiece when in the storage condition.

4. The inhaler housing according to claim 3, wherein the lower end of the receiving portion is dome shaped.

5. The inhaler housing according to claim 1, wherein the at least one protrusion of the dispensing portion comprises a pair of protrusions, and the at least one channel of the receiving portion comprises a pair of channels, wherein the pair of channels are configured to respectively receive the pair of protrusions, the pair of protrusions and the pair of channels defining the limit of movement between the storage condition and the use condition.

6. The inhaler housing according to claim 1, wherein the receiving portion is substantially tubular.

7. The inhaler housing according to claim 1, wherein the receiving portion includes a bore extending along at least a portion of a length of the receiving portion.

8. The inhaler housing according to claim 1, wherein the dispensing portion at least partially overlies the receiving portion when the inhaler housing is in the storage condition.

9. The inhaler housing according to claim 1, wherein, to move the inhaler housing from the storage condition to the use condition, a first movement in a form of the sliding movement followed by a second movement in a form of the pivotal movement of the receiving portion relative to the dispensing portion is required.

10. The inhaler housing according to claim 1, wherein the mouthpiece of the dispensing portion is provided with an external cover member.

11. The inhaler housing according to claim 1, wherein, in the use condition, the dispensing portion and the receiving portion are oriented at an angle of between about 80° and about 110° to one another.

12. The inhaler housing according to claim 1, wherein the receiving portion includes one or more connection members adapted to allow connection of the inhaler housing to an item of clothing, a bag, or a belt.

13. The inhaler housing according to claim 1, wherein the receiving portion includes an actuation portion adapted to assist in the dispensing of the medicament from the container.

14. The inhaler housing according to claim 1, wherein the extension is oriented at an angle of between about 60° and about 120° with respect to a longitudinal axis of the channel.

15. The inhaler housing according to claim 14, wherein the extension is oriented at an angle of about 90° with respect to the longitudinal axis of the channel.

16. The inhaler housing according to claim 1, wherein pivotal movement of the dispensing portion with respect to the receiving portion causes the protrusion to move into the extension.

* * * * *